United States Patent [19]

Allen

[11] Patent Number: 4,540,842

[45] Date of Patent: Sep. 10, 1985

[54] REMOVAL OF SULFUR COMPOUNDS FROM PENTANE

[75] Inventor: George C. Allen, Odessa, Tex.

[73] Assignee: El Paso Products Company, Odessa, Tex.

[21] Appl. No.: 571,312

[22] Filed: Jan. 16, 1984

[51] Int. Cl.³ .......................... C07C 7/12; C07C 7/13; C10G 29/00

[52] U.S. Cl. .................... 585/823; 585/822; 208/250

[58] Field of Search ............... 585/822, 823; 208/250; 55/75, 74, 76

[56] References Cited

U.S. PATENT DOCUMENTS

| | | | |
|---|---|---|---|
| 2,309,871 | 2/1943 | Schulze et al. | 585/822 |
| 2,577,824 | 12/1951 | Stine | 208/250 |
| 2,618,586 | 11/1952 | Hendel | 208/250 |
| 2,700,690 | 1/1955 | Mottern | 208/250 |
| 2,748,059 | 5/1956 | Nixon | 208/250 |
| 2,765,914 | 10/1956 | Seyfried | 585/823 |
| 2,877,176 | 3/1959 | Wolff | 585/823 |
| 3,051,646 | 8/1962 | Brooke | 208/250 |
| 3,080,436 | 3/1963 | King et al. | 585/823 |
| 3,278,624 | 10/1966 | Thomas, Jr. | 585/823 |
| 3,310,595 | 3/1967 | Molinet | 585/823 |
| 4,098,684 | 7/1978 | Innes | 585/823 |
| 4,313,821 | 2/1982 | Gorwood | 208/250 |

*Primary Examiner*—D. E. Gantz
*Assistant Examiner*—Helane Myers
*Attorney, Agent, or Firm*—Fred S. Valles; Margareta LeMaire

[57] ABSTRACT

Pentane derived from fractionation of sulfur-containing natural gasoline is desulfurized to low levels of sulfur, e.g., 1 ppm or below, in a process comprised of contacting the pentane in a first zone with molecular sieve adsorbent to remove dimethylsulfide and then in a second zone with activated carbon to remove carbon disulfide.

8 Claims, No Drawings

REMOVAL OF SULFUR COMPOUNDS FROM PENTANE

BACKGROUND OF THE INVENTION

Because of its low octane rating and, therefore, low value as a motor fuel blending component, natural gasoline is advantageously fractionated into narrower boiling cuts, which have specialized applications and are often considerably more valuable than the natural gasoline feed. For instance, the pentane fraction or the separated fractions of n-pentane and iso-pentane, are useful as blowing agents in the preparation of foamed plastics. One requirement of blowing agents are that they be odor free and, therefore, desulfurization is required when the natural gasoline feed contains odoriferous sulfur compounds. Generally, such a desulfurization includes a caustic wash of either the natural gasoline feed or the pentane fraction(s) obtained by distillation of the gasoline. This caustic wash removes the mercaptans as is well known in the art. In the distillation to produce the narrow pentane fraction dimethyl sulfide remains with the pentane produced even after rectification because of the proximity of their respective boiling points (dimethylsulfide: 37.5° C., n-pentane: 36.1° C.). A convenient method for removing dimethylsulfide from the pentane product is by adsorption onto molecular sieves. In most cases, the combined caustic wash treatment and molecular sieve absorption will result in an odor-free pentane product containing usually less than 1 ppm of sulfur.

However, in some cases there still remains a problem with sulfur contamination of pentane fractions even after rigorous distillations, caustic washings and molecular sieve treatments which theoretically should be sufficient to remove any organic sulfur compounds boiling in the vicinity of the pentane boiling point.

It is therefore an object of this invention to provide a process for the substantially complete desulfurization of pentane.

THE INVENTION

In accordance with the present invention there is provided a process for the desulfurization of pentane which comprises contacting pentane in a first contacting zone with molecular sieve adsorbent, contacting pentane from said first zone with activated carbon in a second contacting zone and recovering a substantially sulfur-free pentane product from said second zone.

In experiments leading up to the present invention, it was found unexpectedly that carbon disulfide was the source of the problem with residual sulfur remaining in the pentane after caustic wash and molecular sieve treatment. This could not be anticipated since carbon disulfide boils at 46° C. which is considerably above the boiling points of 36° C. for n-pentane and 28° C. for iso-pentane. This contaminant would not have been expected to be present in the narrow-boiling pentane cut obtained in the fractionation of natural gasoline. It was also found in high reflux distillation experiments that unexpectedly the carbon disulfide contaminant is a "light-end" to pentane. Using a 70-tray column and a 120:1 reflux the carbon disulfide concentration increased in the overhead and decreased in the bottoms, giving a strong indication of the existence of an azeotrope of pentane and carbon disulfide.

The feed to the process of this invention is a pentane which can be either n-pentane, isopentane or a mixture thereof, and it is provided substantially free of hydrogen sulfide and mercaptans. Any method capable of removing such sulfur contaminants may be used in treating either the pentane fraction or the entire natural gasoline stock from which the pentane fraction is derived. Preferably, the method should be as simple as possible and in most cases a conventional caustic wash employing a 5-15 wt % caustic solution is adequate in removing the aforementioned sulfur contaminants from the hydrocarbon phase. The caustic treatment is usually followed by one or more water washes.

The resulting pentane from the caustic wash typically containing less than 5 ppm of residual hydrogen sulfide and mercaptans is then treated with molecular sieve for the removal of dimethylsulfide, which usually is the main sulfur contaminant remaining after the caustic wash. Any residual amounts of hydrogen sulfide and mercaptans are removed in this treatment step which, in addition, removes water remaining from previous washing steps. The adsorption can be carried out in batchwise fashion by agitating the pentane and molecular sieve and then filtering the mixture to remove the molecular sieve. Preferably, however, the adsorption is carried out in a continuous fashion feeding the pentane to one end of one or more serially connected stationary packed beds of the molecular sieve material.

The molecular sieve should be selected from any of those known to perform well in sweetening of light hydrocarbon liquids. These materials are well known and commercially available in various forms, e.g., as powders, pellets and granuales.

The liquid hourly space velocity LHSV is usually maintained in a range from about 0.5 to about 8 volumes of pentane per hour per volume of molecular sieve bed. Ambient temperatures are used in the process step and sufficient pressures to ensure that the pentane is maintained in liquid phase during treatment.

The intermediate product removed from the outlet of the molecular sieve treatment zone is subsequently passed to a second treatment zone where it is contacted with activated carbon for removal of carbon disulfide by adsorption. The contacting can be carries out batchwise or in continuous fashion similar to the procedures discussed previously in connection with the molecular sieve contacting. Again, the activated carbon contacting is preferably conducted in a continuous fashion feeding the pentane to one end of one or more serially connected stationary beds of activated carbon, each of at least about 5 feet length.

The activated carbon can be selected from any of those manufactured for liquid phase applications, e.g., activated carbon made from lignite, coal, bones, wood, peat or papermill waste. It can be used either as powders, granules or pellets.

The pentane liquid hour space velocity LHSV is usually maintained between about 0.5 and 8 vol. pentane per vol. of adsorbent per hour but lower and higher space velocities may also be used. Other operating conditions such as temperature and pressure are generally in the same range as those employed in the molecular sieve contacting zone.

Regeneration of the molecular sieve bed is carried out periodically or when the adsorption capacity of the molecular sieve has been nearly exhausted. Such regenerations usually involve draining the pentane from the bed, which is then purged with an inert gas such as nitrogen at atmospheric or elevated pressures and at elevated temperatures for several hours.

The procedure employed for the regeneration of used activated carbon is similar to the molecular sieve regeneration procedure and need not be discussed in any further detail.

In large scale continuous operations it is preferable to utilize two or more columns for each adsorbent operated in parallel such that adsorption and regeneration can be carried out simultaneously without disturbing the continuity of the operation.

In order to provide a better understanding of the invention reference is made to the following examples:

EXAMPLES 1-6

Pentane desulfurization experiments were conducted in a unit which essentially consisted of two serially connected packed beds, each contained in a 5'9"×1½" Schedule 40 stainless steel pipe. The molecular sieve bed was packed by pouring in 4" of glass beads followed by 5' of type 13×molecular sieve granules obtained from Union Carbide. The rest of the space (5") was packed with glass beads. The charcoal bed was packed by pouring in 5" of glass beads followed by 5' of 8×30 mesh bituminous coal charcoal (surface area about 1000 sq. m./g) obtained from Calgon. The rest of the space (4") was packed with glass beads. The beads used were 5 mm in diameter. Both beds had stainless-steel screens on the ends to hold the packing down. Each of the beds were equipped with heaters for use during regeneration/activation of the adsorbents.

Liquid pentane feed, about 50% normal and 50% iso-pentane, was pumped at ambient temperature, and at a desired flow rate from a feed tank upwards through the molecular sieve bed to remove dimethylsulfide, then upwards through the charcoal bed to remove carbon disulfide and product was collected from said last bed. Breakthrough of sulfur contaminants (i.e., a contaminant concentration of 1 ppm or more) was monitored by sampling the products from both beds every half hour. The flow of pentane was discontinued when breakthrough of dimethylsulfide or carbon disulfide occurred in the charcoal bed and the beds were then regenerated. After draining pentane from the bed and flow lines the beds were separately dried by purging with nitrogen at ambient temperatures. After blocking off the connection between the beds, the adsorbents were separately regenerated by first gradually heating to an inlet temperature of about 600° F. and an outlet temperature of about 490° F., while passing 144 SCFH of atmospheric nitrogen through each bed, and when the outlet reached about 490° F. the system was switched to nitrogen at 140 psi which was passed at a rate of 90 SCFH for 5 hours through the molecular sieve bed, while the conditions employed in the charcoal bed were respectively 455 SCFH for 3 hours. Heating of the beds were discontinued and atmospheric nitrogen was used to cool the beds, now ready for another treatment cycle.

The feed to each experiment contained varying amounts of sulfur contaminants as indicated in Table 1. In most cases, the feed had been spiked with dimethylsulfide and carbon disulfide to obtain the indicated concentrations. In Experiment 2, the carbon disulfide was actually added in amount more than 100 times normally found in untreated pentane fractions from distillations of natural gasoline. Table 1 also tabulates other pertinent data from the experimentation. The results show that it is possible and feasible to remove sulfur contaminants from commercially distilled pentane to less than 1 ppm. The capacity for dimethylsulfide is in the range of 21–35 mg per cc of bed for 350–3000 ppm in pentane feed and the capacity for carbon disulfide is in the range of 0.10–0.24 mg per cc of bed for 11–35 ppm, in pentane feed.

It is to be understood that many modifications and alterations can be made to the process of this invention without departing from its scope, which is defined by the specification and appended claims.

TABLE 1

| Experiment No. | 1 | 2 | 3 | 4 | 5 | 6 |
|---|---|---|---|---|---|---|
| Feed | | | | | | |
| Sulfur analysis: | | | | | | |
| Dimethyl Sulfide - ppm | 350 | 400 | 1400 | 2800 | 3000 | 2300 |
| Carbon disulfide - ppm | — | 1569 | 12 | 11 | 31 | 35 |
| Others - ppm | 0.7 | — | — | — | — | — |
| Flow Rate - cc/min | 60 | 100 | 30 | 30 | 30 | 30 |
| LHSV in each bed | 1.8 | 3.0 | 0.9 | 0.9 | 0.9 | 0.9 |
| Breakthrough (a) | | | | | | |
| Kg of pentane treated | | | | | | |
| Dimethyl Sulfide: | | | | | | |
| Mole Sieve (b) | 118 | 109 | 33 | 25.3 | 22.5 | — |
| Total (c) | 130 | 118 | 36.7 | 27.5 | 28.4 | — |
| Carbon disulfide (d) | — | 4.7 | 16.6 | 16.6 | 15.4 | 7.8 |
| Mg of sulfur compound adsorbed per cc of bed: | | | | | | |
| Dimethyl Sulfide (e) | 20.7 | 21.7 | 23.2 | 35.5 | 33.7 | — |
| Carbon disulfide (f) | — | 3.7 | 0.100 | 0.091 | 0.238 | 0.136 |

(a) Breakthrough of a contaminant occurs when 1 ppm or more shows up in product
(b) Kg of product from charcoal bed at breakthrough of dimethyl sulfide in mole sieve bed
(c) Kg of product from charcoal bed at breakthrough of dimethyl sulfide in chrcoal bed
(d) Kg of product from charcoal bed at breakthrough of carbon disulfide in charcoal bed
(e) Mole sieve bed
(f) Charcoal bed

What is claimed is:

1. A process for the removal of carbon disulfide and other sulfur contaminants from pentane which comprises:
   contacting pentane in a first contacting zone with an adsorbent consisting essentially of molecular sieve; contacting pentane from said first zone in a second contacting zone with an adsorbent consisting essentially of activated carbon, and recovering pentane product substantially free of carbon disulfide and other sulfur contaminants from said second zone.

2. The process of claim 1 wherein the first contacting zone comprises a stationary packed bed of molecular sieve adsorbent.

3. The process of claim 1 wherein the second contacting zone comprises a stationary packed bed of activated carbon.

4. The process of claim 1 wherein the recovered pentane product contains no more than 1 ppm of carbon disulfide and other sulfur contaminants.

5. The process of claim 1 wherein the pentane has been subjected to a caustic wash prior to contacting with molecular sieve adsorbent.

6. The process of claim 1, wherein the pressure in each of said first and second contacting zones is sufficient to maintain the pentane in liquid phase.

7. The process of claim 2, wherein the pentane liquid hourly space velocity in the first contacting zone is between about 0.5 and about 0.8 vol/vol/hr.

8. The process of claim 3 wherein the pentane liquid hourly space velocity in the second contacting zone is between about 0.5 and about 8 vol/vol/hr.

* * * * *